United States Patent [19]

Nose et al.

[11] 4,402,940

[45] Sep. 6, 1983

[54] METHOD FOR TREATING BLOOD PLASMA EMPLOYING A HOLLOW FIBER MEMBRANE

[75] Inventors: Yukihiko Nose, Cleveland; Koji Kayashima, Mayfield; Akinori Sueoka, South Euclid, all of Ohio; Yoshihiro Asanuma, Sendai, Japan; Shigeru Shinagawa; James Smith, both of Cleveland, Ohio; Andrej Werynski, Warsaw, Poland; Paul S. Malchesky, Painesvilla Township, Lake County, Ohio

[73] Assignee: Kuraray Co., Ltd., Kurashiki, Japan

[21] Appl. No.: 418,551

[22] Filed: Sep. 17, 1982

[30] Foreign Application Priority Data

Mar. 12, 1982 [JP] Japan ................................ 57-39696

[51] Int. Cl.$^3$ ............................................. A61K 35/14
[52] U.S. Cl. .................................... 424/101; 128/1 R
[58] Field of Search ......................................... 424/101

[56] References Cited

U.S. PATENT DOCUMENTS 3,002,887 10/1961 Zilliken ............................. 424/101
4,321,192 3/1982 Jain ................................... 424/101

*Primary Examiner*—Sam Rosen
*Attorney, Agent, or Firm*—Barry Kramer

[57] ABSTRACT

This invention provides a method for treating blood plasma wherein a hollow fiber membrane which comprises at least a skin layer on one surface of the membrane and also a porous layer inside the membrane is employed. The skin layer of the membrane has micropores with average pore size of 50 to 450 Å, and the membrane shows a water permeability of 80 ml/m$^2$.hr.mmHg or more, and permeabilites for human blood plasma albumin of 85% or more and for human blood plasma immunoglobulin G(IgG) of 80% or more, and a rate of inhibition against human blood plasma immunoglobulin M(IgM) of 40% or more. Use of the above mentioned hollow fiber membrane, which makes it possible to selectively remove immune complex, rheumatoid factors, etc., without decrease in levels of immunological functions, brings excellent effects on therapy of autoimmune diseases.

8 Claims, 8 Drawing Figures

METHOD FOR TREATING BLOOD PLASMA EMPLOYING A HOLLOW FIBER MEMBRANE

BACKGROUND OF THE INVENTION

1. Field of the Invention

The present invention relates to a method for treating blood plasma effective in treating autoimmune diseases, wherein a hollow fiber membrane which makes it possible to selectively remove immune complex, rheumatoid factors, etc., is employed.

2. Description of the Prior Art

Various methods of treating blood such as hemofiltration with filter membranes, hemoperfusion with adsorptive agents, etc., in addition to hemodialysis using dialysis membrane have been widely employed in a field of clinical medicine. Further, a technique which is called plasma-pheresis is being developed recently as a method for treating blood by extracorporeal circulation. In the plasmapheresis, blood is first separated into blood plasma components and blood cell components and the separated blood plasma components are treated in various methods in order to remove disease factors. More particularly, there are two methods of the plasmapheresis, one is a blood plasma substitution method in which blood plasma products made of blood plasma of other persons is substituted for the separated blood plasma component, and the other is a specific plasma component permeation method wherein the separated blood plasma component is further fractionated by a suitable method and then only specific fraction which induces problems is removed and other fractions are returned to the circulation in the body. As a therapeutic method, the blood plasma substitution method does not seem to be a preferable one, because, in the method, large amounts of blood plasma products are necessary as the whole amount of the plasma component of a patient is exchanged and therefore the method becomes expensive, and vicious influences may be brought as blood plasma products can not completely supplement each physiological substance in the plasma. Meanwhile, in the specific plasma component permeation blood, since only some parts of the blood plasma are removed and the other is taken back to the circulation in the body, the above mentioned problems of the former method are much improved. Thus, this method may be said to be a better therapeutic method.

There are already several studies and reports on such a specific plasma component permeation method as mentioned above. For example, there is a report on a method for treating the blood plasma using ethylenevinyl alcohol copolymer membrane (see Japanese Journal of Medical Instrumentation Vol. 49, Suppl. 259–261 (1979)). However, the ethylene-vinyl alcohol copolymer membrane disclosed therein inhibits permeation of 80 to 90% of dextran with a molecular weight of 100,000 as shown in FIG. 3 on page 261 of the Journal and has a water permeability of 20 to 34 ml/1.2 m².hr.mmHg (about 17 to 28 ml/m²./hr.mmHg) which is considerably low.

On the other hand, a method wherein a membrane having micropores with average diameters of 0.05 to 0.20µ piercing through the membrane and distributed uniformly on its surface and having a water permeability at a very high level of 2 l/m².hr.mmHg or more is used for filtering blood plasma is described in Japanese Patent Laid Open Nos. 75163/1981 and 751 64/1981. However, such a membrane having large pores has defects that it cannot efficiently filter and differentiate low-density lipoprotein (LDL) containing a large amount of cholesterol (molecular weight: 1,300,000 to 3,200,000), human blood plasma innumoglobulin M (molecular weight: about 950,000), and proteins with a molecular weight of some 2,000,000 or less which are not precipitated by cooling (immune complex or the like).

SUMMARY OF THE INVENTION

It is an object of the present invention to provide an improved method for treating blood plasma, wherein hollow fiber membrane comprising at least a skin layer on one surface of said membrane and a porous layer inside the membrane is used. Said hollow fiber membrane is composed of a skin layer having micropores with average pore size of 50 to 450 Å, a porous layer with pores of average size of 500 to 15,000 Å, and shows void volume of 50 to 85%, and a water permeability of 80 ml/m².hr.mmHg or more, and shows permeabilities for human blood plasma albumin of 85% or more and for human blood plasma immunoglobulin G(IgG) of 80% or more, and a rate of inhibition against human blood plasma immunoglobulin M(IgM) of 40% or more. Therefore, as shown in examples to be described later, use of the hollow fiber membrane having said properties in treating the blood plasma makes it possible to inhibit permeation of noxious components such as IgM (molecular weight: about 950,000), cholesterols, immune complexes or rheumatoid factors without loss of albumin and IgG (molecular weight: about 160,000) which are effective components of the blood plasma. In other words, since immune complexes rheumatoid factors or the like can be selectively removed from the blood plasma without reduction in levels of immunological performances by using said hollow fiber membrane, use of the membrane is remarkably effective in the therapy of autoimmune diseases.

BRIEF DESCRIPTION OF THE DRAWING

Nos. 1 to 4 of FIG. 1 are scanning electron photomicrographs at a magnification of 12,000 X showing the structure of the hollow fiber membrane for treating the blood plasma to be used in the method according to the present invention. No. 1 shows a broken section of the exterior surface of the hollow fiber membrane, No. 2 is the exterior surface of the membrane, No. 3 is a broken section of the interior surface of the membrane, and No. 4 is the interior surface of the membrane.

DETAILED DESCRIPTION OF THE INVENTION

Figure 1:
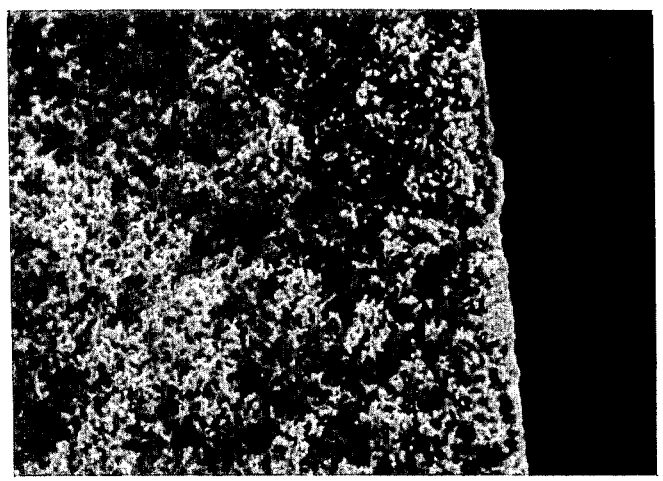
Figure 1:
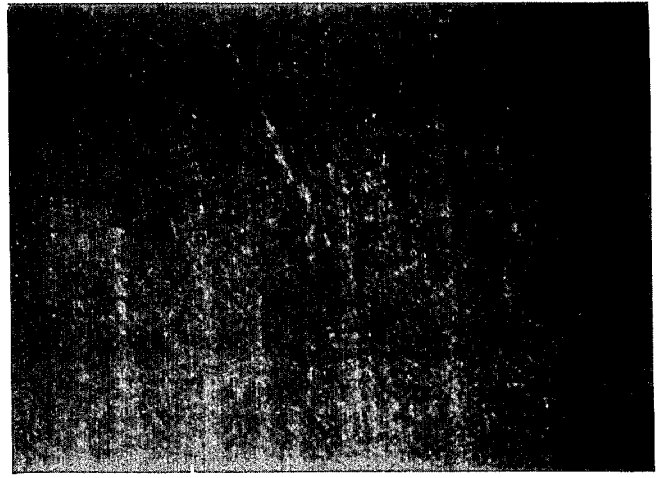
Figure 1:
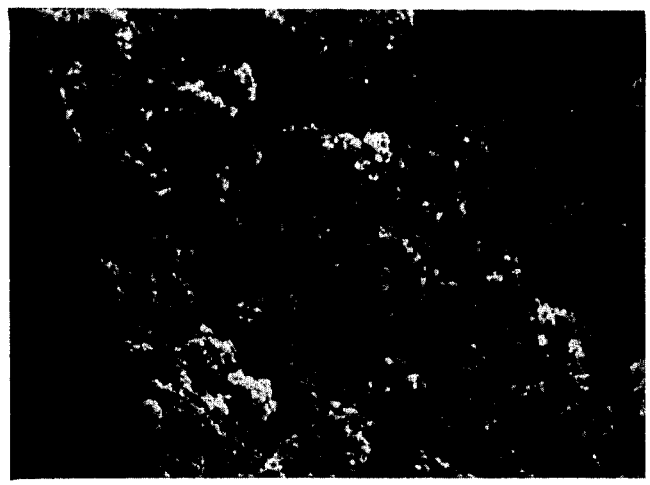
Figure 1:

A hollow fiber membrane to be used in the present invention comprising at least a relatively dense microporous layer (a skin layer) on one surface of the membrane and a porous supporting layer (a porous layer) inside the hollow fiber is (1) one which has a relatively dense microporous layer (a skin layer) on the exterior surface of the hollow fiber membrane and porous supporting layer (a porous layer) both inside and on the interior surface of the membrane, (2) one which has a relatively dense microporous layer on the interior surface of the membrane and a porous supporting layer both inside and on the exterior surface of the membrane, or (3) one which has a relatively dense microporous layer on both interior and exterior surfaces of the membrane and a porous supporting layer inside it. When the blood plasma is treated by pouring it into the inner side of the membrane, a membrane of an asymmetrical structure which has a relatively dense microporous layer on the exterior surface and a porous supporting layer both inside and on the interior surface of the membrane is most desirable because of its constantly high cut-off performance and water permeability which are brought about by the porous supporting layer lying both inside and on the interior surface of the membrane which plays a role of a prefilter for huge molecules such as fibrinogen, thereby preventing clogging of pores of the relatively dense microporous layer on the exterior surface.

Further, the hollow fiber membrane to be used in the present invention has a water permeability of 80 ml/m$^2$.hr. mmHg or more, offering an advantage that treatment of the blood plasma is completed in a relatively short time. When the water permeability is at a level of 80 ml/m$^2$.hr. mmHg or less, treating the blood plasma by the extracorporeal circulation requires a long time, resulting in a severe burden for patients. A higher level of water permeability is so much preferable, and from the standpoint of clinical practices, most desirable levels of the permeability are in the rage of 150 ml/m$^2$.hr.mmHg or higher. The proper upper limit of the permeability is approximately 1,500 ml/m$^2$.hr.mmHg.

Moreover, because said hollow fiber membrane has a cut-off performance exemplified by permeabilities for human blood plasma albumin of 85% or more, for IgG of 80% or more, and a rate of inhibition against IgM of 40% or more, the membrane permits penetration of albumin and IgG in the blood plasma and inhibits penetration of cholesterols and IgM as mentioned above. Still preferred cut-off performances are exemplified by permeabilities for human blood plasma albumin and IgG of 95% or more and 90% or more, respectively, and a rate of inhibition against IgM of 50% or more.

Void volume of this hollow fiber membrane is in the range of 50 to 85%. When the void volume is 50% or lower, a water permeability of 80 ml/m$^2$.hr.mmHg or more can hardly be obtained as the membrane resistance becomes too strong, and when it is 85% or higher, pressure resistance of the membrane becomes insufficient. Preferred void volume ranges from 55 to 80%.

Said hollow fiber membrane has another characteristic that its porous supporting layer both inside and on the interior surface of the membrane has micropores with average diameters of 500 to 15,000 Å. The porous supporting layer with such micropores has a large influence on the water permeability and cut-off performance. When average diameters of micropores are 500 Å or less, the membrane resistance becomes strong and it becomes difficult to gain a water permeability at a high level and when they are 15,000 Å or more, the membrane can not give the prefilter effect mentioned before on chylomicron, fibrinogen or the like and the pressure resistance of the membrane is apt to be insufficient. Shapes of the micropores in the porous supporting layer may be a network, fine voidful, honeycomb, or granular structure. The porous supporting layer may optionally contain cavities or finger-like pores.

The thinness of said membrane is also one of its characteristics. The thickness of the membrane can be freely selected in the range of 10 to 200$\mu$, preferably 10 to 90$\mu$, and still preferably 10 to 60$\mu$. As the membrane becomes thinner, the water permeability becomes higher advantageously. When the membrane is 10$\mu$ thick or less, it is difficult to maintain a pressure resistance at a level of 500 mmHg necessary for extracorporeal circulation. The inside diameter of the hollow fiber membrane can be selected in the range of 50 to 800$\mu$, preferably in the range of 100 to 500$\mu$.

The relatively dense microporous layer on the exterior surface of the hollow fiber membrane to be used in a method of the present invention greatly influences permeability for water and other substances, has micropores of average core size of 50 to 450 Å, and is 100 to 30,000 Å thick. It is preferred that the relatively dense microporous layer forms a thin-film structure which is oriented in the longitudinal direction of the membrane. The micropores of the relatively dense microporous layer are preferred to have average diameters ranging from 200 to 400 Å, and have average thicknesses ranging from 500 to 10,000 Å. Among vinyl alcohol polymers such as polyvinyl alcohol or an ethylene-vinyl alcohol copolymer, polyacrylonitrile, polymethyl methacrylate, cellulose (cupro-ammonium cellulose, acetyl cellulose, etc.), or polysulfone which are used as the raw material of said hollow fiber membrane, the ethylene-vinyl alcohol copolymer to be mentioned later in Examples are preferred.

The ethylene-vinyl alcohol copolymer especially suitable for use as the raw material of the hollow fiber membrane to be employed in a method of the present invention are described hereinafter.

Said ethylene-vinyl alcohol copolymer may be a random, block or graft copolymer. When the ethylene content of the copolymer is 10 mol% or less, wet mechanical properties of the resulting membrane are insufficient and amounts of eluates therefrom undesirably increase, and the ethylene content of 90 mol% or more induces undesirable decrease in biocompatibility and permeability of the membrane. Therefore, ethylene contents of the copolymer of 10 to 90 mol%, especially 15 to 60 mol%, are preferable. Such ethylene-vinyl alcohol copolymer is distinguished from polyvinyl alcohol in that amounts of eluates are very small, and therefore suitable for use as a material for making membrane for hemodialysis to be conducted in the medical field. Regarding the degree of saponification of the ethylene-vinyl alcohol copolymer, unless it is 80 mol% or more, wet mechanical properties of the resulting membrane are insufficient. The degree of saponification of 95 mol% or higher is especially preferred. Usually, an ethylene-vinyl alcohol copolymer with the degree of saponification of 99 mol% or higher which means a substantially complete saponification is used. The ethylenevinyl alcohol copolymer may contain 15 mol% or less of copolymerizable monomers such as methacrylic acid, vinyl chloride, methyl methacrylate, acrylonitrile or vinylpyrrolidone, may be cross-linked by the treatment of said copolymer, before or after forming the membrane, with an inorganic cross-linking agent such as a boron compound or organic cross-linking agent such as a diisocyanate or dialdehyde, or may be acetalized at functional hydroxyl groups in the vinyl alcohol unit with an aldehyde such as formaldehyde, acetaldehyde, butylraldehyde or benzaldehyde to an extent not more than 30 mol%. It is preferable to use an ethylene-vinyl alcohol copolymer having a viscosity value ranging from 1.0 to 50 cP as measured in a solution in dimethyl sulfoxide with a concentration of 3% by weight at a temperature of 30° C. with the use of a Brookfield viscometer. When the viscosity is lower than the level mentioned above, namely, when the degree of polymerization is lower, mechanical properties necessary as a membrane can not be obtained and when the viscosity is higher than said level, formation of the membrane gets difficult. The membrane of the ethylene-vinyl alcohol copolymer to be used in a method of the present invention can be obtained by forming a membrane from said ethylene-vinyl alcohol copolymer in a method to be described later.

Said ethylene-vinyl alcohol copolymer membrane has a skin layer (relatively dense microporous layer) on one or both surfaces of the membrane, and said skin layer controls mainly permeability and cut-off performances of the membrane. Though it is extremely difficult to clarify microstructure of the skin layer, electron microscopic observations of a dry membrane disclosed that the layer had micropores with diameters ranging from 50 to 450 Å.

The skin layer with said structure has a porous supporting layer thereunder. The porous layer affords a sort of barrier for the skin layer and therefore the structure of the porous layer has great influences upon performances of the membrane.

A method for manufacturing the hollow fiber membrane to be used in a method of the present invention will now be described. Said ethylene-vinyl alcohol copolymer membrane is obtained by dissolving an ethylene-vinyl alcohol copolymer with an ethylene content of 10 to 90 mol% in a solvent comprising at least one compound selected from the group consisting of dimethyl sulfoxide, dimethylacetamide, methylpyrrolidone and pyrrolidone, to obtain a solution with a polymer concentration (C) of 10 to 40% (by weight), and by feeding the resulting polymer solution into a coagulation bath chiefly consisting of water, to form a membrane.

Selection of coagulation temperature is especially important for obtaining a membrane suitable for a method of the present invention. A close relation exists between the polymer concentration (C) and coagulation temperature (T) and the purpose ethylene-vinyl alcohol copolymer membrane can be obtained when the relation is defined in the following range;

$C-10 \leq T \leq C+30$, preferably $C-8 \leq T \leq C+15$

Solvents for dissolving said ethylene-vinyl alcohol copolymer may be a monohydric alcohol such as methanol or ethanol, a polyhydric alcohol such as ethylene glycol, propylene glycol, or glycerol, phenol, m-cresol, methylpyrrolidone, formic acid, and those containing water. Among these, the one selected from the group of dimethyl sulfoxide, dimethyl-acetamide, methylpyrrolidone, pyrrolidone and mixtures of said substances are suitable for manufacturing a separating membrane having well-balanced water and solute permeabilities which is to be obtained in a method of the present invention. Especially, dimethyl sulfoxide which can dissolve the ethylene-vinyl alcohol copolymer therein at a high level is preferable.

In dissolving the ethylene-vinyl alcohol copolymer in said solvent, its concentration is in the range of 10 to 40% by weight, preferably 15 to 35% by weight. Further, the temperature of the polymer solution is 0° to 120° C., preferably 5° to 60° C. When the temperature of the solution is above said range, the polymer is liable to be denatured, while when it is below said level, the viscosity of the stock solution becomes so high that the membrane formation becomes difficult.

In the coagulation bath, an aqueous medium is used as a coagulating agent. The aqueous medium may be water alone, an aqueous solution containing a water-miscible organic solvent, usually the same as one used for preparing the polymer solution, in a range of not more than 70% by weight, or said aqueous solution to which is further added an inorganic salt such as Glauber's salt. The membrane can be manufactured above a gelation temperature of the stock solution in a wet coagulation process or in a dry/wet process where the stock solution is fed into a coagulation bath after passing air or solvent vapor. After the coagulation, wet heat processing, elongation, drying or the like, can be employed if necessary. The membrane can be used in a wet state, or after dried, and it is desirable to use it after drying in view of easy handling. Methods for drying the membrane may be drying under normal or reduced pressure below a glass transition point of the ethylene-vinyl alcohol copolymer, more preferably at around room temperature, freeze-drying where water contained in the wet membrane is sublimated under reduced pressure after freezing the membrane with liquid nitrogen, etc., or an organic solvent replacement method where a water-miscible organic solvent is first replaced for water contained in the membrane and then the solvent is removed by vaporization.

In the organic solvent replacement method, a permeable membrane which maintains its permeable performance is obtained by dipping the wet membrane in a water-miscible organic solvent to replace for an aqueous medium present on the surface or inside of the membrane, and drying the resulting membrane below a glass transition point of the ethylene-vinyl alcohol copolymer, preferably at room temperature, under normal or reduced pressure. In this method, lower aliphatic alcohols or ketones having 1 to 5 carbon atoms are preferred organic solvents and, for example, methanol, ethanol, amyl alcohol, acetone, methyl ethyl ketone, or diethyl ketone can be used. Among them, acetone is particularly preferable. Drying of the resulting membrane after the replacement process is carried out below a glass transition point of the copolymer. In another way where said organic solvent is not used for replacing for water, a membrane which can maintain the permeability after formation is obtained by treating the undried membrane below 50° C. with an aqueous or alcoholic solution of a polyhydric aliphatic alcohol containning 2 to 4 carbon atoms or an adduct obtained by adding 1 to 20 mol of ethylene oxide to said alcohol, and then drying the resulting membrane below 50° C.

In this method, the resulting membrane contains, in a ratio of 20 to 120%, the polyhydric alcohol or ethylene oxide adduct of said alcohol which can be easily removed from the membrane by washing after its construction into a module and before use. The polyhydric aliphatic alcohols having 2 to 4 carbon atoms may be ethylene glycol, diethylene glycol, propylene glycol, 1,3-butanediol, 1,4-butanediol, or glycerol, and glycerol is especially desirable. Said polyhydric aliphatic alcohols may also be added to a coagulating liquid to be used in a wet method for manufacturing the membrane and thus incorporated in the resulting membrane.

When said membrane is actually used for treating the blood by extracorporeal circulation, the blood taken out of the artery is first devided into blood cells and blood plasma components using plasma separator (a membrane which inhibits permeation of blood cells and platelets but which permits permeation of blood plasma components, for example, a module provided with a hollow fiber membrane, or an apparatus equipped with a centrifugal separator) and the separated blood plasma component is introduced into a blood plasma treating equipment provided with a hollow fiber membrane to inhibit high molecular substances such as cholesterols, immune complexes and IgM and to take back albumin and IgG which has permeated the membrane into the vein together with blood cell components. In this case, fluid replacement (for example, albumin and hydroxyethyl starch) may also be introduced into the vein, if necessary. General conditions under which the blood plasma is treated by yhe extracorporeal circulation using said hollow fiber membrane are flow rate of the blood plasma of 10 to 500 ml/min, temperature of $-2°$ to $45°$ C., and transmembrane pressure (TMP) of 0 to 2 kg/cm$^2$, preferably 10 to 300 mmHg, and treating time of usually 2 to 4 hours.

Blood plasma treatment mentioned above makes it possible to suitably and effectively treat such diseases as systemic lupus erythematosus, malignant articular rheumatism, familial hypercholesterolemia, or Goodpasture's syndrome.

In the application of the invention, levels of water permeability, void volume, microstructure, permeability and inhibition performance are determined as follows;

(1) Water permeability of the membrane, K', was obtained by the determination at a temperature of 37° C. under a transmembrane pressure of 20 to 100 mmHg.

$$K' = V/A \cdot t \cdot \Delta P (ml/m^2 \cdot hr \cdot mmHg)$$

V: volume of water permeated(ml),
A: area of the membrane (m$^2$)
t: permeation time(hr)
$\Delta P$: transmembrane pressure under which the determination is conducted(mmHg)

(2) Void volume was calculated from the following formula:

$$\left(1 - \frac{P_D}{P_W}\right) \times 100(\%)$$

PD: weight of dry membrane
PW: weight of water-containing membrane (measured after removal of water on the surface of the membrane which has been dipped in water in a dried state, prior to the measurement, to have water sufficiently penetrate into micropores, and then taken out from there.)

(3) Microstructures were examined by scanning electron photomicrographs. Diameters of micropores of the relatively dense microporous layer were calculated using cutoff rate for standard proteins and water permeability.

(4) Rates of permeability and inhibition were determined under conditions of a solute concentration of 0.1%, temperature of 37° C., TMP of 20 mmHg, QB of 200 ml/min, and membrane area of 1 m$^2$.

The present invention will be better understood by the following examples.

EXAMPLE 1

A solution with a polymer concentration of 22% was prepared by dissolving a saponificated ethylene-vinyl acetate copolymer with an ethylene content of 33% and the degree of saponification of 99.8% in dimethyl sulfoxide at a temperature of 80° C. and removing bubbles at the same temperature. The resulting spinning solution is extruded through a ring spinneret along with N$_2$gas, at a constant rate of 0.42 ml/min from an orifice for outflow of an internal coagulating agent provided at the middle of the spinneret and is coagulated in a 20% aqueous solution of dimethyl sulfoxide (at a temperature of 20° C.). Then, after washing the coagulating agent with hot water and replacing acetone for water contained in the resulting fiber, the fiber was dried at a temperature of 25° C. The obtained hollow fiber has an inside diameter of 220$\mu$, an outside diameter of 320$\mu$, and a membrane thickness of 50$\mu$ in a dry state. Microstructures of the obtained hollow fiber membrane were examined by a scanning electron microscope.

Methods and results of the examinations are as follows Method: Broken sections were prepared by bending the hollow fiber membrane while cooling with liquid nitrogen. Then, after vacuum deposition of alloy of gold and palladium on the resulting broken sections, their photographs were taken with a scanning electron microscope, as shown in Nos. 1 and 4 of FIG. 1.

Nos. 1 and 2 of FIG. 1 show a broken section on the exterior surface side of the membrane and the exterior surface of the membrane, respectively, at a magnification of 12,000 X. From these figures, it is understood that, on the exterior surface of the membrane there is a thin-film structure oriented in the longitudinal direction of the hollow fibers and that there is a porous supporting layer (with an average pore size of 800 Å) under the relatively dense microporous layer about 2,000 Å thick. An average diameter of micropores of the relatively dense microporous layer was found to be approximately 400 Å by calculation using cut-off rate for standard proteins and water permeability. Nos. 3 and 4 of FIG. 1 show a broken section on the interior surface side of the membrane and the inner surface of the membrane, respectively, at a magnification of 12,000 X. From these figures, a porous supporting layer (with an average pore size of about 800 Å) was found to exist both inside and on the inner surface of the membrane.

The hollow fiber membrane had a void volume of 58%, water permeability of 240 ml/mmHg.m$^2$.hr (for pure water at a temperature of 37° C.), permeabilities for human blood plasma albumin and IgG of 89% and 85%, respectively, and a rate of inhibition against IgM of 52%.

A module (with an effective membrane area of 1 m$^2$) was produced by bundling 6,500 hollow fibers mentioned above and fixing both ends of the resulting fiber bundle to a cylindrical housing with a polyurethane resin. An apparatus shown in FIG. 2 was constructed of said module, blood pump, manometer, blood circuit and the like, and the blood plasma which was kept at a temperature of 37° C. was circulated in the apparatus at a flow rate of 20 ml/min. 15 minutes after starting the circulation, a $Q_{out}$ valve was fully closed and filtration was started. The blood plasma used in experiments was 1 l of normal human blood plasma containing tool protein, ablumin, IgG, IgM, total cholesterol, and fibrinogen in quantities of 5.4 g/dl, 3.5 g/dl, 640 mg/dl, 49 mg/dl, 110 mg/dl, and 160 mg/dl, respectively. By the time of termination of the 2-hour blood plasma filtration with both $Q_{in}$ (quantity of the blood plasma introduced) and $Q_{UF}$ (quantity of the blood plasma filtered) each kept at a constant rate of 20 ml/min, pressure ($P_i$) increased gradually from an initial level of 10 mmHg to 120 mmHg and was thereafter kept at an almost constant rate. Rate of removal for each component in 1 l of the blood plasma, (1-(concentration after t minutes/initial concentration))×100, changed as shown in FIG. 3. From these results, it is understood that IgM, cholesterols, fibrinogen, or the like can be separated and removed from the blood plasma with a bare decrease in levels of albumin and IgG.

Figure 2:
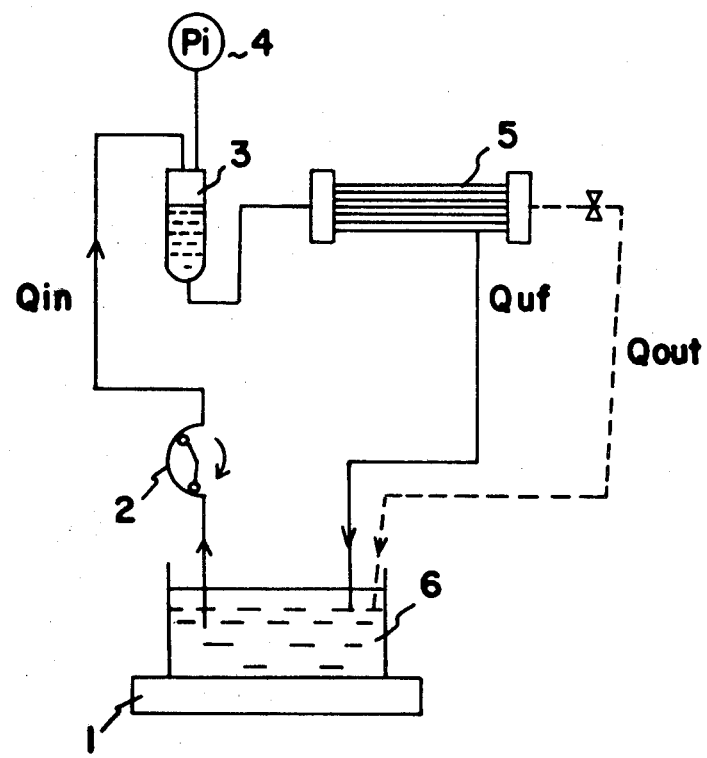
FIG. 2 shows a system for treating the blood plasma, wherein a hollow fiber membrane module for treating the blood plasma is employed.
Figure 3:
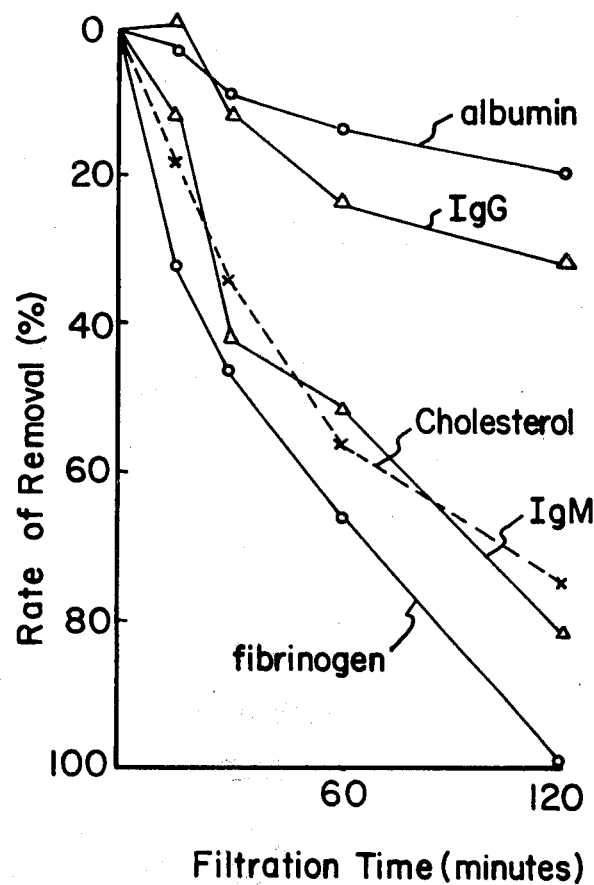
FIG. 3 is a graph showing changes in rates of removal of normal human blood plasma components with time using said hollow fiber membrane.

In FIG. 2 reference numeral 1 represents a heater-magnetic stirrer, 2 is a pump, 3 is a bubble removing and pressure supervisory apparatus, 4 is a pressure gage, 5 is a blood plasma filter (module), and 6 is blood plasma. In FIG. 3, the ordinate shows the rate of removal, (1-(concentration after t minutes/initial concentration))×100, and the abscissa shows filtration time (minutes) t.

EXAMPLE 2

Figure 4:
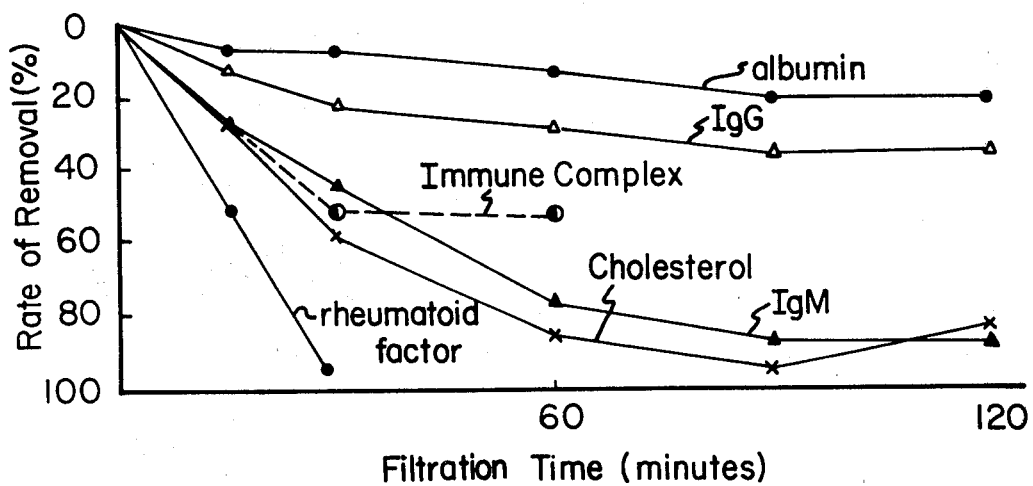
FIG. 4 is a graph showing changes in rates of removal of blood plasma components of a patient suffering from rheumatism with time using said hollow fiber membrane.

0.73 l of the blood plasma of a patient of rheumatism was filtered by circulating it in the same apparatus as in Example 1 equipped with the same module as in Example 1. Starting under conditions of $Q_{in}$ of 84 ml/min, $Q_{UF}$ of 20 ml/min, and $P_i$ of 10 mmHg, filtration was conducted for 2 hours with $Q_{in}$ and $Q_{UF}$ kept at a constant rate. Value of $P_i$ when the filtration was finished was 46 mmHg. The blood plasma before filtration contained total protein, albumin, IgG, IgM, total cholesterol, rheumatoid factors, and immune complex (Clq binding type) in quantities of 2.8 g/dl, 1.5 g/dl, 340 mg/dl, 80 mg/dl, 41 mg/dl, 225 RLS, and 124 units, respectively. Rates of removal for each component changed with time as shown in FIG. 4. From the figure, it was disclosed that the removal of rheumatoid factors, cholesterols, and immune complex (Clq binding type) was effectively carried out.

COMPARATIVE EXAMPLE

In the same manner for manufacturing a hollow fiber membrane as in Example 1 except that the temperature of a cogulation bath was kept at 10° C., a hollow fiber having, in a dry state, inside and outside diameters of 210 and 290µ, respectively, and a membrane thickness of 40µ was obtained. The resulting fiber further had an average pore size of about 450 Å on the interior surface and of about 70 Å on the exterior surface, void volume of 70%, water permeability of 40 ml/mmHg.m².hr, permeabilities for human blood plasma albumin and IgG of 50% and 40%, respectively, and a rate of inhibition against IgM of 98%.

Figure 5:
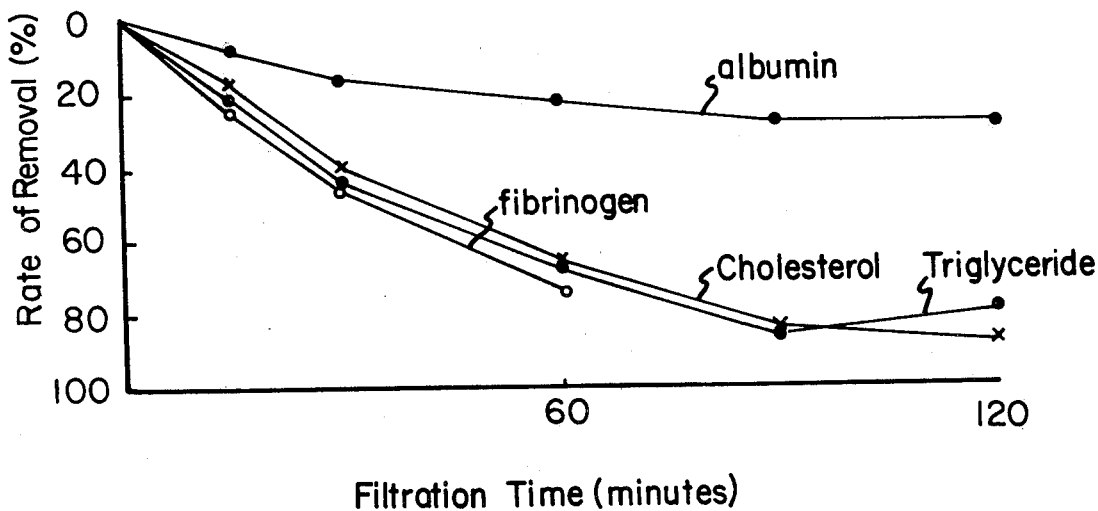
FIG. 5 is a graph showing changes in rates of removal of normal human blood plasma components with time using a hollow fiber membrane according to a Comparative Example.

A module was produced by bundling 6,800 hollow fibers mentioned above in the same method as in Example 1, and 10 l of normal human blood plasma was filtered by circulation in the same way as in Example 2. $P_i$ was 10 mmHg at the beginning and increased to 360 mmHg when the filtration was finished. As shown in FIG. 5, rates of removal for each component in the blood plasma increased, and therefore though it was at least possible to separate albumin from other substances such as cholesterol, the velocity of permeation was as slow as one third or less of that in Example 1 and pressure ($P_i$) was also not on a level suitable for the extracorporeal circulation.

What is claimed is:

1. A method for treating the blood plasma to selectively reduce the amount of a disease factor therein comprising fractionating the plasma with a hollow fiber membrane comprising a skin layer on at least one surface of said membrane and a porous layer inside said membrane with average pore size of micropores of said skin layer in the range of 50 to 450 Å, that of micropores of the porous layer ranging from 500 to 15,000 Å, void volume of said membrane at a level of 50 to 85% and water permeability at a level of 80 ml/m².hr.mmHg or higher, such that the amount of the disease factor in one of the fractions produced is decreased.

2. A method for treating the blood plasma as claimed in claim 1, wherein said hollow fiber membrane has a skin layer on its exterior surface and a porous supporting layer both inside and on the interior surface of said membrane.

3. A method for treating the blood plasma as claimed in claim 1 or claim 2, wherein said hollow fiber membrane shows permeabilities for human blood plasma albumin and human blood plasma immunoglobulin G of 85% or more and 80% or more, respectively, and a rate of inhibition against human blood plasma immunoglobulin M of 40% or more.

4. A method for treating the blood plasma as claimed in any one of claims 1 to 3, wherein the skin layer of said hollow fiber membrane is 100 to 30,000 Å thick.

5. A method for treating the blood plasma as claimed in any one of claims 1 to 4, wherein thickness of the hollow fiber membrane ranges 10 to 90µ and inside diameter thereof is in the range of 50 to 800µ.

6. A method for treating the blood plasma as claimed in any one of claims 1 to 5, wherein water permeability is in the range of 80 to 1,500 ml/m².hr.mmHg.

7. A method for treating the blood plasma as claimed in any one of claims 1 to 6, wherein the hollow fiber membrane is composed of a vinyl alcohol polymer.

8. A method for treating the blood plasma as claimed in claim 7, wherein said vinyl alcohol polymer is an ethylene-vinyl alcohol copolymer.

* * * * *